US012721629B2

(12) United States Patent
Li et al.

(10) Patent No.: US 12,721,629 B2
(45) Date of Patent: Sep. 1, 2026

(54) DUAL-LUMEN OCCLUSION BALLOON CATHETER AND METHOD OF USE

(71) Applicant: VASCUPATENT MEDICAL (SHENZHEN) CO., LTD, Shenzhen (CN)

(72) Inventors: Jiaming Li, Shenzhen (CN); Lizhong Lu, Shenzhen (CN)

(73) Assignee: VascuPatent Medical (Shenzhen) Co., Ltd., Shenzhen (CN)

(*) Notice: Subject to any disclaimer, the term of this patent is extended or adjusted under 35 U.S.C. 154(b) by 215 days.

(21) Appl. No.: 18/363,799

(22) Filed: Aug. 2, 2023

(65) Prior Publication Data

US 2024/0041466 A1 Feb. 8, 2024

(30) Foreign Application Priority Data

Aug. 2, 2022 (CN) ........................ 202210921663.1

(51) Int. Cl.

*A61B 17/12* (2006.01)
*A61M 25/00* (2006.01)
*A61M 25/10* (2013.01)

(52) U.S. Cl.

CPC .. *A61B 17/12136* (2013.01); *A61B 17/12109* (2013.01); *A61B 2017/1205* (2013.01);

(Continued)

(58) Field of Classification Search

CPC ........ A61B 17/12022; A61B 17/12136; A61B 17/1204; A61B 17/12036;

(Continued)

(56) References Cited

U.S. PATENT DOCUMENTS 5,176,698 A * 1/1993 Burns ................. A61M 25/104 606/192
5,728,065 A * 3/1998 Follmer ................ A61M 25/10 604/96.01

(Continued)

OTHER PUBLICATIONS

"ePTFE Porosity"—International Polymer Engineering, 2019, https://ipeweb.com/fluoroflex-eptfe/eptfe-porosity (Year: 2019).*

*Primary Examiner* — Darwin P Erezo
*Assistant Examiner* — Mitchell Brian Hoag

(57) ABSTRACT

The present disclosure provides double-lumen closure balloon catheter, including an inner tube and an outer tube. A distal end of the inner tube extends from a distal end of the outer tube, the inner tube is provided at its distal end with a tubular hydrophobic tip through which air passes, a cavity of the hydrophobic tip is in communication with a cavity of the inner tube, the outer tube is provided at its distal end with an expandable or shrinkable balloon, a proximal end of the balloon is hermetically coupled to the distal end of the outer tube, a distal end of the balloon is hermetically coupled to the hydrophobic tip, and a channel in communication with an inner cavity of the balloon is arranged between the inner tube and the outer tube. The present disclosure further provides a using method thereof. As compared with the related art, the liquid is injected into the channel so as to push air in the inner cavity of the balloon and the channel to the hydrophobic tip and then discharge air in the cavity of the hydrophobic tip through the wall of the hydrophobic tip. As a result, it is able to prevent the balloon from being damaged, and facilitate the operation, thereby to reduce the time for the surgery.

15 Claims, 1 Drawing Sheet

(52) U.S. Cl.
CPC ............... *A61M 2025/0039* (2013.01); *A61M 2025/1061* (2013.01)

(58) Field of Classification Search
CPC .... A61B 17/12031; A61M 2025/1077; A61M 2025/1061; A61M 2025/0039
See application file for complete search history.

(56) References Cited

U.S. PATENT DOCUMENTS 6,221,042 B1 * 4/2001 Adams .................... A61F 2/958 604/96.01
6,379,373 B1 * 4/2002 Sawhney .............. A61M 31/00 606/193
10,588,768 B2 * 3/2020 Nelson .................. A61M 39/22
2002/0177867 A1 * 11/2002 Hebert .............. A61M 25/1006 606/192
2005/0197667 A1 * 9/2005 Chan ................. A61M 25/1025 604/97.01
2010/0217313 A1 * 8/2010 Raabe .............. A61B 17/12136 606/213
2011/0152905 A1 * 6/2011 Eaton .................. A61M 25/104 606/159
2012/0078096 A1 * 3/2012 Krolik ................ A61M 25/1011 604/28
2014/0379021 A1 * 12/2014 Krishnan ......... A61B 17/12136 606/194
2018/0001063 A1 * 1/2018 Aggerholm ....... A61M 25/1034
2018/0049873 A1 * 2/2018 Manash ................ A61M 25/09
2019/0167331 A1 * 6/2019 Schultheis ............. A61B 18/02
2019/0321593 A1 * 10/2019 Crawford .......... A61M 25/0097
2019/0388112 A1 * 12/2019 Nguyen ........... A61B 17/12109
2020/0001055 A1 * 1/2020 Pigott ................. A61M 25/104
2020/0046230 A1 * 2/2020 McCaffrey ........... A61B 5/6851
2020/0054352 A1 * 2/2020 Brouillette ....... A61B 17/22012
2020/0108234 A1 * 4/2020 Sanati ................... A61M 29/02
2020/0146858 A1 * 5/2020 Wolenberg ......... A61M 25/1011
2020/0254229 A1 * 8/2020 Proxenos .......... A61M 25/1002
2020/0289136 A1 * 9/2020 Chou ...................... A61B 17/22
2020/0353229 A1 * 11/2020 Casey ............. A61M 25/10185
2020/0360026 A1 * 11/2020 Horton ............. A61B 17/12122
2021/0045806 A1 * 2/2021 Yagi ................... A61B 18/1492
2022/0047267 A1 * 2/2022 Johnston ............. A61M 1/3655
2022/0273323 A1 * 9/2022 Baron ................... A61M 1/774
2023/0035425 A1 * 2/2023 Ghuge ................. A61B 18/245
2023/0071144 A1 * 3/2023 Reynolds .......... A61M 25/0053
2024/0315724 A1 * 9/2024 Mazzone ............... A61B 90/39
2025/0065080 A1 * 2/2025 Magnin ............. A61M 25/0068

* cited by examiner

DUAL-LUMEN OCCLUSION BALLOON CATHETER AND METHOD OF USE

TECHNICAL FIELD

The present disclosure relates to medical equipment, in particular to a double-lumen closure balloon catheter and a using method thereof.

BACKGROUND

Clinical statistics show that, in all cerebrovascular diseases, the incidence of intracranial aneurysm is smaller than those of cerebral thrombosis and hypertensive cerebral hemorrhage, more than 150,000 patients with arterial aneurysm occur in China every year, and about 30% of these patients are dead in the initial rupture of intracranial aneurysm. When the patient survives fortunately, the rupture of aneurysm may probably occur, leading to rehemorrhage. At this time, a death rate is about 60% to 70%, and usually any integral multiple of 7 days is a high-risk rupture stage.

For a balloon-assisted coiling technique, antiplatelet therapy is not required during the surgery, so it is able to provide protection, remodel an aneurysmal neck, and reduce the damage caused by the secondary rupture of arterial aneurysm in embolization.

Currently, balloon-assisted embolization is an important method in the interventional embolization of intracranial aneurysm. Usually, a double-lumen closure balloon catheter is used, and a distal end of a balloon is closed through high-temperature steam. For a conventional closure balloon catheter (as shown in FIG. 1), the distal end of the balloon is opened in a normal state, and it is not hermetically coupled to an inner tube. Before the surgery, a distal end of the inner tube is closed through a J-shaped shaping needle, the balloon is enclosed by a wet gauze (to prevent the balloon from being damaged due to a high temperature), and the gauze at the distal end of the balloon is pinched by hand. The high-temperature steam is provided at a position close to a tip and the balloon, so as to shrink the balloon and enable the distal end of the balloon to be hermetically fixed to a wall of the inner tube at the distal end, thereby to enable the balloon to be in a hermetical state (as shown in FIG. 2). The catheter is cooled at a normal temperature for 1 minute, and then the J-shaped shaping needle is extracted. However, the balloon is easily damaged by the high-temperature steam. In addition, the operation of the catheter is complicated, and it takes a long time period to discharge the air.

SUMMARY

An object of the present disclosure is to provide a double-lumen closure balloon catheter and a using method thereof, so as to prevent the balloon from being damaged and reduce the time for the surgery.

In one aspect, the present disclosure provides in some embodiments a double-lumen closure balloon catheter, including an inner tube, and an outer tube sleeved onto the inner tube and arranged coaxially with the inner tube, a catheter holder being arranged at a proximal end of the catheter. A distal end of the inner tube extends from a distal end of the outer tube, the inner tube is provided at its distal end with a tubular hydrophobic tip through which air passes, a cavity of the hydrophobic tip is in communication with a cavity of the inner tube, the outer tube is provided at its distal end with an expandable or shrinkable balloon, a proximal end of the balloon is hermetically coupled to the distal end of the outer tube, a distal end of the balloon is hermetically coupled to the hydrophobic tip, a channel in communication with an inner cavity of the balloon is arranged between the inner tube and the outer tube, and after a liquid is injected into the channel, air in the inner cavity of the balloon and the channel is pushed to the hydrophobic tip and discharged from the cavity of the hydrophobic tip through a wall of the hydrophobic tip.

In a possible embodiment of the present disclosure, the hydrophobic tip is made of a waterproof, air-permeable film.

In a possible embodiment of the present disclosure, the waterproof, air-permeable film is made of expanded polytetrafluoroethylene.

In a possible embodiment of the present disclosure, the wall of the hydrophobic tip has a thickness of 0.005 mm to 0.2 mm.

In a possible embodiment of the present disclosure, a first metallic ring is tightly sleeved at a joint between the balloon and the hydrophobic tip.

In a possible embodiment of the present disclosure, a second metallic ring is tightly sleeved at a joint between the hydrophobic tip and the inner tube.

In a possible embodiment of the present disclosure, a second metallic ring is tightly sleeved at a joint between the hydrophobic tip and the inner tube.

In a possible embodiment of the present disclosure, the liquid is injected into the channel at a pressure smaller than 14.7 psi.

In another aspect, the present disclosure provides in some embodiments a method for using the above-mentioned double-lumen closure balloon catheter, including: discharging air in the inner cavity of the balloon and the channel in vitro before surgery; and injecting a filling medium into the channel during the surgery so as to fill up the balloon with the filling medium. The discharging air in the inner cavity of the balloon and the channel in vitro before surgery includes enabling the hydrophobic tip to face up, enabling an injector filled with a liquid to be coupled to the proximal end of the outer tube, and injecting the liquid into the channel through the injector, so that the liquid and air are pushed into the inner cavity of the balloon and air at the distal end of the balloon is discharged from the cavity of the hydrophobic tip through the wall of the hydrophobic tip.

In a possible embodiment of the present disclosure, the filling medium is injected into the channel during the surgery at a pressure smaller than 14.7 psi.

According to the embodiments of the present disclosure, as compared with the related art, the hydrophobic tip with micropores is arranged at the distal end of the inner tube, and the liquid is injected into the channel so as to push air in the inner cavity of the balloon and the channel to the hydrophobic tip and then discharge air in the cavity of the hydrophobic tip through the wall of the hydrophobic tip. As a result, it is able to prevent the balloon from being damaged, and facilitate the operation, thereby to reduce the time for the surgery.

DETAILED DESCRIPTION

The present disclosure will be described hereinafter in conjunction with the drawings and embodiments.

In the embodiments of the present disclosure, the term "distal end" refers to an end away from an operator, and the term "proximal end" refers to an end close to the operator.

Figure 3:
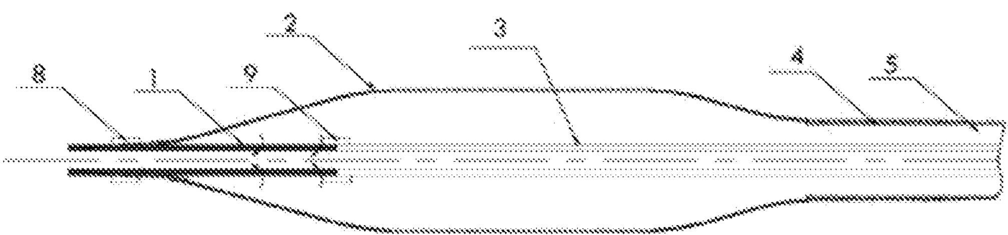
FIG. 3 is a schematic view showing a double-lumen closure balloon catheter according to one embodiment of the present disclosure.

As shown in FIG. 3, the present disclosure provides in some embodiments a double-lumen closure balloon catheter, which includes an inner tube 3, and an outer tube 4 sleeved onto the inner tube 3 and arranged coaxially with the inner tube 3. A distal end of the inner tube 3 extends from a distal end of the outer tube 4, the inner tube 3 is provided at its distal end with a tubular hydrophobic tip 1 which have micropores and through which air passes, a cavity of the hydrophobic tip 1 is in communication with a cavity of the inner tube 3, and the cavity of the inner tube 3 and the cavity of the hydrophobic tip 3 together form a passage for a guide wire. In addition, the cavity of the hydrophobic tip 1 further serves as an exhaust passage for discharging air. The outer tube 4 is provided at its distal end with an expandable or shrinkable balloon 2, a proximal end of the balloon 2 is hermetically coupled to the distal end of the outer tube 4, and a distal end of the balloon 2 is hermetically coupled to the hydrophobic tip 1. A channel 5 in communication with an inner cavity of the balloon 2 is arranged between the inner tube 3 and the outer tube 4. The channel 5 is used for the injection of a liquid, so as to fill the balloon 2 up with the liquid, e.g., water. After the liquid is injected into the channel 5, air in the inner cavity of the balloon 2 and the channel 5 is pushed to the hydrophobic tip 1 and discharged, under the effect of a pressure, from the cavity of the hydrophobic tip 1 through a wall of the hydrophobic tip 1.

Figure 4:
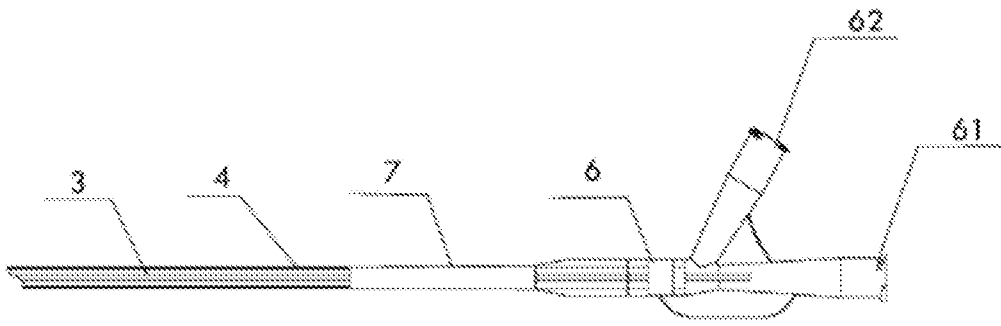
FIG. 4 is a schematic view showing a proximal end of the catheter according to one embodiment of the present disclosure.

As shown in FIG. 4, a catheter holder 6 is arranged at a proximal end of the catheter, and a stress-relieving tube 6 is arranged at a proximal end of the catheter holder 6. The catheter holder 6 is detachably coupled to the stress-relieving tube 7, and it is a hollow solid of revolution. To be specific, the catheter holder is attached to the stress-relieving tube 7 through an ultraviolet (UV)-curable adhesive.

In a possible embodiment of the present disclosure, the catheter holder 6 is a Y-shaped solid of revolution, and it includes a first taper 61 and a second taper 62. The first taper 61 is straight and has a cone-shaped cavity. A bottom end of the cone-shaped cavity faces the proximal end of the first taper 61 to serve as a locking taper, and the proximal end of the first taper 61 is coupled to a Luer taper to form a guide wire cavity. A distal end of the first taper 61 is in communication with the cavity of the inner tube 3. The second taper 62 is oblique, a distal end of the second taper 62 serves as a locking taper, and a proximal end of the second taper 62 is coupled to a Luer taper to form a liquid injection cavity. The second taper 62 is in communication with the channel 5. The stress-relieving tube 7 is a tubular solid of revolution, and it is sleeved onto the proximal end of the outer tube 4 and coupled to the distal end of the catheter holder 5, so as to improve the strength at a joint between the catheter holder and the catheter, thereby to prevent the catheter from being bent at the proximal end.

In the embodiments of the present disclosure, the hydrophobic tip 1 is made of a waterproof, air-permeable film, e.g., expanded polytetrafluoroethylene (ePTFE).

The wall of the hydrophobic tip 1 has a thickness of 0.005 mm to 0.2 mm. Water passes through the wall of the hydrophobic tip 1 when a pressure of water is greater than or equal to 14.7 psi. When the pressure is smaller than 14.7 psi, air, rather than water, is allowed to pass through the wall of the hydrophobic tip 1. In the embodiments of the present disclosure, the liquid is injected into the channel 5 at a pressure smaller than 14.7 psi, so as to prevent the liquid from entering arteries.

Figure 1:
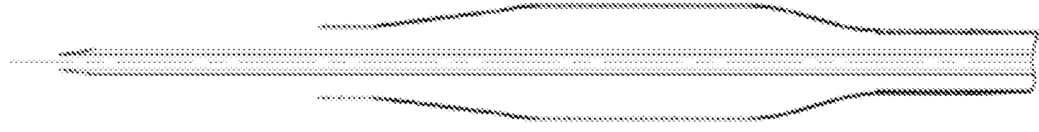
FIG. 1 is a schematic view showing a conventional closure balloon catheter in a normal state.
Figure 2:
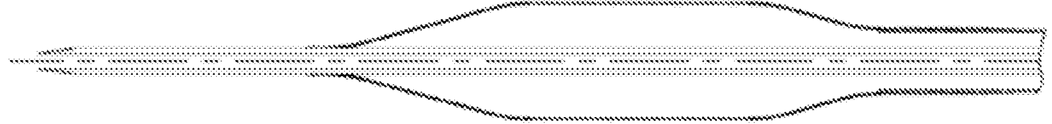
FIG. 2 is a schematic view showing the conventional closure balloon catheter when a distal end of the balloon is closed through high-temperature steam.

As shown in FIG. 1, in the related art, the outer tube 4 is fixed to the balloon 2 through welding, e.g., heat sealing or laser welding. In the embodiments of the present disclosure, the balloon 2 is coupled to the hydrophobic tip 1 through a curable adhesive, and a first metallic ring 8 is arranged at a joint between the balloon and the hydrophobic tip, so as to improve the strength. In addition, the hydrophobic tip 1 is also coupled to the inner tube 3 through a curable adhesive, and a second metallic ring 9 is arranged at a joint between the hydrophobic tip and the inner tube.

The present disclosure further provides in some embodiments a method for using the above-mentioned double-lumen closure balloon catheter, which includes: discharging air in the inner cavity of the balloon and the channel in vitro before surgery; and injecting a filling medium into the channel during the surgery so as to fill up the balloon with the filling medium. The discharging air in the inner cavity of the balloon and the channel in vitro before surgery includes enabling the hydrophobic tip 1 to face up, enabling an injector filled with a liquid to be coupled to the proximal end of the outer tube 4, and injecting the liquid into the channel 5 through the injector, so that the liquid and air are pushed into the inner cavity of the balloon 2. A density of air is smaller than a density of the liquid, so air is pushed by the liquid to the distal end of the balloon 2, and then discharged from the cavity of the hydrophobic tip 1 through the wall of the hydrophobic tip 1. Because the injection pressure of the liquid is smaller than the pressure under which the liquid is allowed to pass, after the discharging of air, the balloon is filled up with the filling medium (e.g., a mixture of normal saline and a contrast medium) without any leakage.

According to the embodiments of the present disclosure, the hydrophobic tip with micropores is arranged at the distal end of the inner tube, and the liquid is injected into the channel so as to push air in the inner cavity of the balloon and the channel to the hydrophobic tip and then discharge air in the cavity of the hydrophobic tip through the wall of the hydrophobic tip. As a result, it is able to prevent the balloon from being damaged.

The above embodiments are for illustrative purposes only, but the present disclosure is not limited thereto. Obviously, a person skilled in the art may make further modifications and improvements without departing from the spirit of the present disclosure, and these modifications and improvements shall also fall within the scope of the present disclosure.

What is claimed is:

1. A double-lumen closure balloon catheter, comprising:
- an inner tube;
- an outer tube sleeved onto the inner tube and arranged coaxially with the inner tube;
- a catheter holder being arranged at a proximal end of the double-lumen closure balloon catheter, wherein a distal end of the inner tube extends from a distal end of the outer tube; and
- a tubular hydrophobic tip at the distal end of the inner tube, wherein the tubular hydrophobic tip is made of an air-permeable film, the tubular hydrophobic tip has micropores through which air passes, a cavity of the tubular hydrophobic tip is in communication with a cavity of the inner tube, the outer tube is provided at its distal end with an expandable or a shrinkable balloon, a proximal end of the expandable or the shrinkable balloon is hermetically coupled to the distal end of the outer tube, a distal end of the expandable or the shrinkable balloon is hermetically coupled to the tubular hydrophobic tip, a channel in communication with an inner cavity of the expandable or the shrinkable balloon is arranged between the inner tube and the outer tube, and after a liquid is injected into the channel, the air in the inner cavity of the expandable or the shrinkable balloon and the channel is pushed to the tubular hydrophobic tip and discharged from the cavity of the tubular hydrophobic tip through the air-permeable film and the micropores, wherein the tubular hydrophobic tip is a separate, distinct venting structure coupled to the distal end of the inner tube, and is configured to discharge air from the inner cavity of the balloon to the cavity of the inner tube and prevent liquid from passing therethrough during inflation of the balloon.

2. The double-lumen closure balloon catheter according to claim 1, wherein the air-permeable film is waterproof.

3. The double-lumen closure balloon catheter according to claim 1, wherein the air-permeable film comprises expanded polytetrafluoroethylene.

4. The double-lumen closure balloon catheter according to claim 3, wherein the tubular hydrophobic tip has a wall thickness of 0.005 mm to 0.2 mm.

5. The double-lumen closure balloon catheter according to claim 1, wherein a first metallic ring is tightly sleeved at a joint between the expandable or the shrinkable balloon and the tubular hydrophobic tip.

6. The double-lumen closure balloon catheter according to claim 5, wherein a second metallic ring is tightly sleeved at a joint between the tubular hydrophobic tip and the distal end of the inner tube.

7. The double-lumen closure balloon catheter according to claim 1, wherein the air-permeable film is configured to allow air but prevent water passing therethrough at a pressure smaller than 14.7 psi.

8. A method for using the double-lumen closure balloon catheter according claim 1, comprising:

discharging air in the inner cavity of the expandable or the shrinkable balloon and the channel in vitro before surgery;

injecting a filling medium into the channel during the surgery so as to fill up the balloon with the filling medium, wherein the discharging of the air in the inner cavity of the balloon and the channel in vitro before the surgery comprises enabling the tubular hydrophobic tip to face up;

enabling an injector filled with the liquid to be coupled to a proximal end of the outer tube; and injecting the liquid into the channel through the injector, so that the liquid and the air are pushed into the inner cavity of the balloon and the air at the distal end of the expandable or the shrinkable balloon is discharged from the cavity of the tubular hydrophobic tip through the wall of the tubular hydrophobic tip.

9. The method according to claim 8, wherein the filling medium is injected into the channel during the surgery at a pressure smaller than 14.7 psi.

10. The double-lumen closure balloon catheter according to claim 1, wherein the cavity of the tubular hydrophobic tip and the cavity of the inner tube form a passage for a guidewire.

11. The double-lumen closure balloon catheter according to claim 1, further comprising a stress-relieving tube that is arranged at a proximal end of the catheter holder.

12. The double-lumen closure balloon catheter according to claim 11, wherein the catheter holder is attached to the stress-relieving tube through an ultraviolet (UV)-curable adhesive.

13. The double-lumen closure balloon catheter according to claim 1, wherein the tubular hydrophobic tip comprises a proximal end coupled to the distal end of the inner tube within the cavity of the balloon and a distal end extending outside the balloon.

14. The double-lumen closure balloon catheter according to claim 13, wherein the proximal end of the tubular hydrophobic tip is coupled to the distal end of the inner tube via an adhesive.

15. The double-lumen closure balloon catheter according to claim 14, further comprising a second metallic ring tightly sleeved at a coupling joint between the proximal end of the tubular hydrophobic tip and the distal end of the inner tube to strengthen the coupling between the tubular hydrophobic tip and the distal end of the inner tube.

* * * * *